United States Patent
Lee et al.

(10) Patent No.: US 9,642,631 B2
(45) Date of Patent: May 9, 2017

(54) INTERVERTEBRAL PROSTHESIS ENDPLATE HAVING DOUBLE DOME AND SURGICAL TOOLS FOR IMPLANTING SAME

(71) Applicant: K2M, Inc., Leesburg, VA (US)

(72) Inventors: Casey K. Lee, Florham Park, NJ (US); George Makris, West Orange, NJ (US); Alastair J. T. Clemow, Princeton, NJ (US); William F. Ogilvie, Austin, TX (US)

(73) Assignee: K2M, Inc., Leesburg, VA (US)

( * ) Notice: Subject to any disclaimer, the term of this patent is extended or adjusted under 35 U.S.C. 154(b) by 74 days.

(21) Appl. No.: 14/689,007

(22) Filed: Apr. 16, 2015

(65) Prior Publication Data
US 2015/0289888 A1    Oct. 15, 2015

Related U.S. Application Data

(62) Division of application No. 11/862,012, filed on Sep. 26, 2007, now Pat. No. 9,011,542.
(Continued)

(51) Int. Cl.
*A61B 17/16* (2006.01)
*A61F 2/30* (2006.01)
(Continued)

(52) U.S. Cl.
CPC ...... *A61B 17/1671* (2013.01); *A61B 17/1659* (2013.01); *A61F 2/30771* (2013.01);
(Continued)

(58) Field of Classification Search
CPC ................. A61B 17/1659; A61B 17/1671
See application file for complete search history.

(56) References Cited

U.S. PATENT DOCUMENTS

| | | | |
|---|---|---|---|
| 3,867,728 A | 2/1975 | Stubstad et al. | |
| 3,875,595 A | 4/1975 | Froning | |

(Continued)

FOREIGN PATENT DOCUMENTS

| | | | |
|---|---|---|---|
| DE | 42 19 939 A1 | 12/1993 | |
| DE | 201 11 479 U1 | 11/2001 | |

(Continued)

OTHER PUBLICATIONS

Hellier WG et al., Spine 1992, 127(6 Suppl.): Ss86-96.
(Continued)

*Primary Examiner* — Andrew Yang
(74) *Attorney, Agent, or Firm* — Carter, DeLuca, Farrell & Schmidt, LLP

(57) ABSTRACT

An endplate for an intervertebral prosthesis includes a generally planar base plate, a first elevated region, or dome, within the base plate periphery, and a second elevated region, or dome, within the boundary of the first elevated region. The antero-posterior and side-to-side (medial-lateral) dimensions of the first elevated region are made to be unequal in order to provide resistance to torsional stresses, and the laterally opposite sidewalls of the first elevated region are defined by arcs that terminate in sagittal planes of the endplate, and are symmetrical with respect to a coronal plane of the endplate. A bone rasp and a groove cutter for use in implanting the prosthesis are also provided.

5 Claims, 10 Drawing Sheets

Related U.S. Application Data

(60) Provisional application No. 60/847,359, filed on Sep. 27, 2006, provisional application No. 60/847,103, filed on Sep. 26, 2006.

(51) Int. Cl.
*A61F 2/44* (2006.01)
*A61F 2/46* (2006.01)

(52) U.S. Cl.
CPC ............ *A61F 2/442* (2013.01); *A61F 2/4611* (2013.01); *A61F 2002/30069* (2013.01); *A61F 2002/3092* (2013.01); *A61F 2002/30125* (2013.01); *A61F 2002/30563* (2013.01); *A61F 2002/30884* (2013.01); *A61F 2230/0008* (2013.01); *A61F 2230/008* (2013.01)

(56) References Cited

U.S. PATENT DOCUMENTS

| | | |
|---|---|---|
| 4,349,921 A | 9/1982 | Kuntz |
| 4,759,766 A | 7/1988 | Buttner-Janz |
| 4,759,769 A | 7/1988 | Hedman |
| 4,772,287 A | 9/1988 | Ray et al. |
| 4,863,477 A | 9/1989 | Monson |
| 4,904,260 A | 2/1990 | Ray et al. |
| 4,911,718 A | 3/1990 | Lee et al. |
| 4,932,969 A | 6/1990 | Frey et al. |
| 4,946,378 A | 8/1990 | Hirayama et al. |
| 5,047,055 A | 9/1991 | Bao et al. |
| 5,071,437 A | 12/1991 | Steffee |
| 5,123,926 A | 6/1992 | Pisharodi |
| 5,171,281 A | 12/1992 | Parsons et al. |
| 5,190,547 A | 3/1993 | Barber et al. |
| 5,192,326 A | 3/1993 | Bao et al. |
| 5,258,031 A | 11/1993 | Salib et al. |
| 5,306,308 A | 4/1994 | Gross et al. |
| 5,306,309 A | 4/1994 | Wagner et al. |
| 5,314,477 A | 5/1994 | Marnay |
| 5,320,644 A | 6/1994 | Baumgartner |
| 5,370,697 A | 12/1994 | Baumgartner |
| 5,401,269 A | 3/1995 | Buttner-Janz et al. |
| 5,458,642 A | 10/1995 | Beer et al. |
| 5,514,180 A | 5/1996 | Heggeness et al. |
| 5,534,028 A | 7/1996 | Bao et al. |
| 5,534,030 A | 7/1996 | Navarro et al. |
| 5,545,229 A | 8/1996 | Parsons et al. |
| 5,556,431 A | 9/1996 | Büttner-Janz |
| 5,562,738 A | 10/1996 | Boyd et al. |
| 5,674,294 A | 10/1997 | Bainville et al. |
| 5,674,296 A | 10/1997 | Bryan et al. |
| 5,676,702 A | 10/1997 | Ratron |
| 5,683,465 A | 11/1997 | Shinne et al. |
| 5,824,093 A | 10/1998 | Ray et al. |
| 5,824,094 A | 10/1998 | Serhan et al. |
| 5,865,846 A | 2/1999 | Bryan et al. |
| 5,888,226 A | 3/1999 | Rogozinski |
| 5,893,889 A | 4/1999 | Harrington |
| 5,976,186 A | 11/1999 | Bao et al. |
| 6,083,228 A * | 7/2000 | Michelson ......... A61B 17/1659 606/79 |
| 6,113,637 A | 9/2000 | Gill et al. |
| 6,136,031 A | 10/2000 | Middleton |
| 6,139,579 A | 10/2000 | Steffee |
| 6,156,067 A | 12/2000 | Bryan et al. |
| 6,162,252 A | 12/2000 | Kuras et al. |
| 6,187,043 B1 | 2/2001 | Ledergerber |
| 6,187,048 B1 | 2/2001 | Milner et al. |
| 6,224,607 B1 | 5/2001 | Michelson |
| 6,296,664 B1 | 10/2001 | Middleton |
| 6,315,797 B1 | 11/2001 | Middleton |
| 6,348,071 B1 | 2/2002 | Steffee et al. |
| 6,368,350 B1 | 4/2002 | Erickson et al. |
| 6,395,032 B1 | 5/2002 | Gauchet |
| 6,419,704 B1 | 7/2002 | Ferree |
| 6,419,706 B1 | 7/2002 | Graf |
| 6,482,234 B1 | 11/2002 | Weber et al. |
| 6,527,804 B1 | 3/2003 | Gauchet et al. |
| 6,533,818 B1 | 3/2003 | Weber et al. |
| 6,579,320 B1 | 6/2003 | Gauchet et al. |
| 6,579,321 B1 | 6/2003 | Gordon et al. |
| 6,582,466 B1 | 6/2003 | Gauchet |
| 6,582,467 B1 | 6/2003 | Teitelbaum et al. |
| 6,582,468 B1 | 6/2003 | Gauchet |
| 6,592,624 B1 | 7/2003 | Fraser et al. |
| 6,607,558 B2 | 8/2003 | Kuras |
| 6,626,943 B2 | 9/2003 | Eberlein |
| 6,645,248 B2 | 11/2003 | Casutt |
| 6,656,224 B2 | 12/2003 | Middleton |
| 6,669,732 B2 | 12/2003 | Serhan et al. |
| 6,682,562 B2 | 1/2004 | Viart et al. |
| 6,726,720 B2 | 4/2004 | Ross et al. |
| 6,733,532 B1 | 5/2004 | Gauchet |
| 6,740,118 B2 | 5/2004 | Eiserman |
| 6,749,635 B1 | 6/2004 | Bryan |
| 6,793,678 B2 | 9/2004 | Hawkins |
| 6,893,465 B2 | 5/2005 | Huang |
| 7,169,181 B2 | 1/2007 | Kuras |
| 7,250,060 B2 | 7/2007 | Trieu |
| 2001/0016773 A1 | 8/2001 | Serhan et al. |
| 2001/0032017 A1 | 10/2001 | Alfaro |
| 2001/0051829 A1 | 12/2001 | Middleton |
| 2002/0022888 A1 | 2/2002 | Serhan et al. |
| 2002/0077533 A1 | 6/2002 | Bieger et al. |
| 2002/0077701 A1 | 6/2002 | Kuslich |
| 2003/0045939 A1 | 3/2003 | Casutt |
| 2003/0074066 A1 | 4/2003 | Errico |
| 2003/0100951 A1 | 5/2003 | Serhan et al. |
| 2003/0135277 A1 | 7/2003 | Bryan |
| 2003/0164172 A1 | 9/2003 | Chumas et al. |
| 2003/0208271 A1 | 11/2003 | Kuras |
| 2003/0236526 A1 | 12/2003 | Van Hoeck |
| 2004/0002711 A1 | 1/2004 | Berry |
| 2004/0103903 A1 | 6/2004 | Falahee |
| 2004/0122517 A1 | 6/2004 | Kuras et al. |
| 2004/0122518 A1 | 6/2004 | Rhoda |
| 2004/0162563 A1 | 8/2004 | Michelson |
| 2004/0167626 A1 | 8/2004 | Geremakis |
| 2004/0193273 A1 | 9/2004 | Huang |
| 2004/0215197 A1 | 10/2004 | Smith et al. |
| 2004/0249462 A1 | 12/2004 | Huang |
| 2004/0267367 A1 | 12/2004 | O'Neil |
| 2005/0027300 A1 | 2/2005 | Hawkins et al. |
| 2005/0131544 A1 | 6/2005 | Kuras |
| 2005/0273111 A1 | 12/2005 | Ferree |
| 2006/0079907 A1 | 4/2006 | Boettiger |
| 2006/0229724 A1 | 10/2006 | Lechmann |
| 2006/0265075 A1 | 11/2006 | Baumgartner |
| 2006/0276900 A1 | 12/2006 | Carpenter |

FOREIGN PATENT DOCUMENTS

| | | |
|---|---|---|
| EP | 0 566 810 A1 | 10/1993 |
| EP | 0 642 775 A1 | 3/1995 |
| FR | 2 784 291 A1 | 4/2000 |
| GB | 1 496 804 | 1/1978 |
| GB | 1 589 192 | 5/1981 |
| WO | WO 89/03663 A1 | 5/1989 |
| WO | WO 90/11740 A1 | 10/1990 |
| WO | WO 95/19153 A1 | 7/1995 |
| WO | WO 99/22675 A1 | 4/1999 |
| WO | WO 99/22675 A1 | 5/1999 |
| WO | WO 03/090650 A1 | 11/2003 |
| WO | WO 2004/033516 A1 | 4/2004 |
| WO | WO 2004/039291 A1 | 5/2004 |
| WO | WO 2004/054453 A1 | 7/2004 |
| WO | WO 2005/072660 A1 | 8/2005 |
| WO | WO 2005/007041 A1 | 12/2005 |

OTHER PUBLICATIONS

Fraser RD et al., Spine J. 2004, 4(6S): 245s-251s.
Szpalski M, Eur. Spine J. (2000), 11(Suppl.2): S65-84.

(56) References Cited

OTHER PUBLICATIONS

McAfee, P. et al., Spine J. 4:48s, 2004.
Hawkins MV et al., J. Orthop. Res. 12: 119-127, 1994.
Closkey RF et al., Spine 18(8): 1011-1015, 1993.
Langrana NA et al., Spine J. 4 (2004), 245S-251S.
Official Communication dated Oct. 10, 2011, in European Patent Application No. 07 843 237.
Official Communication dated Mar. 12, 2013, in European Patent Application No. 07 843 237.
International Search Report and Written Opinion of the International Searching Authority issued May 13, 2008, in International Patent Application No. PCT/US2007/079557.

\* cited by examiner

INTERVERTEBRAL PROSTHESIS ENDPLATE HAVING DOUBLE DOME AND SURGICAL TOOLS FOR IMPLANTING SAME

CROSS REFERENCE TO RELATED APPLICATION

This application claims the benefit of U.S. Provisional Application No. 60/847,103, filed Sep. 26, 2006, the entire disclosure of which is incorporated herein by reference, and the benefit of U.S. Provisional Application No. 60/847,359, filed Sep. 27, 2006, the entire disclosure of which is incorporated herein by reference.

BACKGROUND OF THE INVENTION

Field of the Invention

This invention relates to prostheses for replacing a human intervertebral disc and instruments for implanting such a prosthesis, and more particularly to an endplate for such a prosthesis having a domed surface for contacting an adjacent vertebra in a human spinal motion segment.

Background Art

The human spinal column achieves its remarkable combination of strong support and appropriate flexibility by reason of its structure comprising bony vertebrae separated by intervertebral discs of softer and flexible tissue that allow limited motion between adjacent vertebrae in flexion-extension, lateral bending, and torsion. Each individual flexible element of the spine, comprising a pair of adjacent vertebrae separated by an intervertebral disc, constitutes a spinal motion segment. The proper function of such a spinal motion segment requires the intervertebral disc to provide proper separation between the vertebrae while allowing sufficient relative motion in the median, coronal and transverse anatomical planes of the body. While each intervertebral disc typically performs its function effectively without conscious awareness, the disc and surrounding tissues are provided with ample innervation that informs the individual of any damage and/or malfunction by providing a pain signal.

The spinal regions most susceptible to painful pathology of the intervertebral disc are the cervical and lumbar regions. Such painful pathology is typically the result of some traumatic injury or age-related changes in the structure and function of the intervertebral disc.

The most common pathologic condition causing chronic low back pain and neck pain is degenerative disc disease (DDD), which is typically the result of age-related changes in the tissues constituting the intervertebral disc, with accompanying abnormalities, e.g., deformation, in the functional structures of the disc. Under such conditions, even normal movement between the adjacent vertebrae can cause pain, which may become chronic and sufficiently severe to result in significant disability. When non-invasive treatment fails to relieve chronic disabling back pain caused by such disease, recourse is had to surgical intervention. For some time, palliative surgical procedures such as disc excision, decompression, and/or spinal fusion have been performed to relieve intractable pain of patients with degenerative disc disease. More recently, artificial intervertebral disc prostheses have been developed, which have made it possible to replace a degenerated disc with such a prosthesis to achieve pain relief and restore anatomical function.

A number of factors must be considered in the design of an intervertebral disc prosthesis if a successful outcome of disc arthroplasty is to be expected. The prosthesis design must provide for proper positioning, correct alignment, congruent contact surface area, and immediate post-operative prosthetic stability within the disc space. In particular, the conformation of the vertebra-contacting surface of the prosthesis at the vertebra-prosthesis interface is of significant importance, particularly for post-operative stability of the prosthesis in the intervertebral space. Experience has shown that the clinical results of intervertebral disc arthroplasty are closely correlated to the proper initial positioning of the disc prosthesis in the disc space and subsequent maintenance thereof. For instance, if an implanted disc prosthesis does not maintain a stable position within the intervertebral space, the patient may experience post-operative accelerated disc degeneration in adjacent spinal motion segments, as well as formation of osteophytic growths on the vertebrae.

Another possible post-operative complication is subsidence of the disc prosthesis into an adjacent vertebra. Such instability is related to at least three factors: contact area between the prosthesis and the adjacent vertebral body, bone mineral density in the contacting surface of the vertebral body, and applied load. In particular, the effective prosthesis-vertebra contact area is affected by the variable curvature and irregular surface profile of the adjacent vertebra, both of which vary significantly from patient to patient, e.g., in the lumbosacral spine which is the site of many intervertebral disc arthroplasties.

The great variety of designs that have been proposed for the bone-contacting surface of intervertebral disc prostheses can be taken as evidence that an ideal design has yet to be achieved. Examples of such prostheses have included those with relatively flat vertebra-contacting surfaces, those with domed profiles, or those incorporating other specially configured shapes such as corrugated or serrated surfaces or protruded platforms.

Besides the general shape of the bone contacting surface, known intervertebral disc prostheses have incorporated additional structures to enhance the security of fixation to the vertebral bone. Some designs have incorporated provisions for fixation using screws driven either into the anterior or lateral sides of the adjacent vertebrae or into the vertebral endplate itself. The bone-contacting surfaces of other prostheses have been provided with spikes, keels, serrations, or the like, in order to provide stable fixation of the prosthesis.

However, certain drawbacks have been observed with the previously known intervertebral disc prostheses. For example, flat prosthetic endplate designs present problems of incongruous fit between the prosthetic endplate and the concave end surface of the vertebral body. Such a mismatch between the shapes can result in post-operative instability of the prosthesis in the disc space, in particular, settling of the prosthesis into the adjacent vertebra (subsidence). Designs that attempt to compensate for this mismatch by providing additional structures such as keel, spikes, and the like incur problems due to the greater distraction between vertebrae required for their implantation. Designs that employ screws placed into the endplates of the vertebrae encounter difficulties in implantation because of the limited working space and the relatively thin bone structures of the vertebral endplates, which do not provide a strong substrate for screw fixation.

Some intervertebral prostheses have incorporated endplates having dome-shaped surfaces for contact with the adjacent vertebral bodies. Both spherical domes and ellipsoidal domes have been employed. Ellipsoidal domes better approximate the planform of a vertebral body, and, when seated in a corresponding ellipsoidal seat reamed in the endplate of the vertebral body, provide a measure of torsional stability. However, preparation of such an ellipsoidal seat and proper alignment with the vertebrae can present some surgical difficulties. Spherical domes, having a circular planform, are more easily fitted to a prepared seat, but, by themselves, tend to provide less torsional stability.

Accordingly, a need has continued to exist for an endplate design that can alleviate the problems experienced in implantation of known intervertebral disc prostheses.

SUMMARY OF THE INVENTION

According to the invention an endplate for an intervertebral disc prosthesis is provided that promotes a stable relationship between the prosthesis and the adjacent vertebrae after implantation. The invention also encompasses tools for preparing a seat or recess in a vertebral body to provide a congruent fit for the endplate of the invention, as well as a surgical procedure for preparing a surgical site and implanting a prosthesis using an endplate of the invention.

The prosthesis endplate of the invention comprises:

a generally planar base plate having a periphery sized and configured to fit within an intervertebral space of a human spinal motion segment;

a first elevated region, or dome, within the base plate periphery, and a second elevated region, or dome, within the boundary of the first elevated region.

The antero-posterior and side-to-side (medial-lateral) dimensions of the first elevated region are made to be unequal in order to provide resistance to torsional movement between the prosthesis endplate and the adjacent vertebral body under the normal stresses produced by the physiological motion of the spinal motion segment. Furthermore, the laterally opposite sidewalls of the first elevated region are defined by arcs that terminate in sagittal planes of the endplate, and are symmetrical with respect to a coronal plane of the endplate. In an alternate embodiment, the arcs terminating the lateral side portions of the first elevated region are circular arcs centered in sagittal planes of the endplate, and may or may not be symmetrical with respect to a coronal plane of the endplate.

The second elevated region is generally dome-shaped, and the laterally opposite side portions are defined by circular arcs having a common center located in the median plane of the endplate.

A bone rasp apparatus for forming a recess or seat in a vertebral body for receiving a prosthesis endplate according to the invention includes at least one bone rasp tool that includes a rasp head and a handle for manipulating the head within an intervertebral space. The rasp head includes a pivot member that can be inserted into a recess formed in the vertebral body endplate rasp teeth arranged on the rasp head to prepare at least a portion of a recess or seat for a vertebral endplate when the rasp head is reciprocally rotated about the pivot member.

A groove-cutter for preparing an antero-posterior groove in a vertebral body to receive a fin or keel of an intervertebral disk prosthesis endplate includes a cutter guide member having a handle and a guide head sized and configured to be seated in a recess or seat previously formed in a vertebral body. The groove-cutter is provided with an antero-posterior guide slot that guides the antero-posterior reciprocating cutter and a stowage recess for stowing the cutter in a protected position while the guide head is inserted into the intervertebral space. The cutter is mounted on a reciprocable and rotatable shaft that actuates the cutter by an antero-posterior reciprocating motion and can be rotated to place the cutter in the stowage recess.

Accordingly, one feature of the invention is an endplate for an intervertebral disc prosthesis that has a dome configuration which provides for improved stability under imposed stresses that tend to produce torsional instability and/or extrusion of the prosthesis from the intervertebral space.

A further feature of the invention is an endplate for an intervertebral disc prosthesis that will facilitate reliable and easy positioning, alignment, preparation of a congruent contact surface, and better stabilization against axial, bending, torsion and translation in the lumbar, lumbosacral or cervical spine.

A further feature of the invention is the formation of a concavity in the vertebral endplate to provide a congruent fit between a domed surface of a prosthesis endplate and the bony vertebral endplate.

A further feature of the invention is a procedure and instrumentation for preparing a generally concave seat in a vertebral endplate to receive an intervertebral prosthesis in order to provide accurate positioning of a prosthesis with maximum sparing of the vertebral bone.

A further feature of the invention is a bone rasp by which a surgeon can accurately form a concave seat for receiving the bone-contacting surface of an intervertebral disc prosthesis using a hand-operated tool that requires only a simple oscillatory motion.

Further features of the invention will be apparent from the description of the invention which follows.

DETAILED DESCRIPTION OF THE INVENTION

Figure 1A:
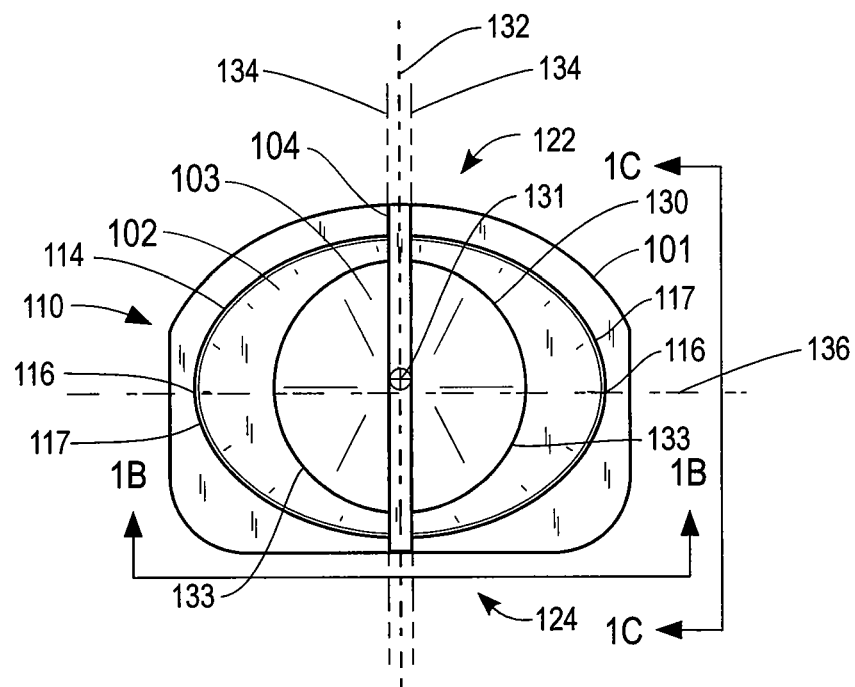
FIG. 1A is a plan view of an intervertebral prosthesis endplate of the invention.

An intervertebral prosthesis designed to replace a degenerated, damaged, or otherwise defective natural intervertebral disc, with retention of at least some of the function of the natural disc, typically incorporates a pair of endplates designed for firm fixation to the adjacent vertebrae of human spinal motion segment, together with some structure separating the endplates and allowing for at least some relative motion therebetween. In the lumbar region of the spine, the minimum contact surface area between these prosthesis endplates and the vertebral bone that is required to prevent subsidence is considered to be approximately 6.5 $cm^2$ for a person with normal bone density. A disc prosthesis endplate having a surface contour (convex) that matches, at least approximately, the generally concave end surface of the adjacent vertebral body that it contacts may be expected to provide a larger endplate-vertebra contact area than a prosthesis endplate with, e.g., a flat, contact surface, thereby achieving a larger surface contact area with corresponding better post-operative stability. When an irregular surface area of the vertebral endplate is reamed to provide a smoother surface, the interface stability and contact surface area can be further improved.

According to the invention an endplate for an intervertebral prosthesis has a generally planar base plate, a first elevated region within the periphery of the base plate, and a second elevated region within the planform of the first elevated region. The first elevated region has an antero-posterior dimension at a median antero-posterior plane and a transverse (or medial-lateral) dimension. These dimensions are made to be unequal, in order to provide for resistance to torsional movement between the endplate and adjacent vertebral body. Typically, because the transverse dimension of a lumbar vertebral body is greater than its antero-posterior dimension, the first elevated region will have a transverse (or medial-lateral) dimension greater than its antero-posterior dimension. That is, the first elevated region can be described as elongated in a lateral direction. Typically, the first elevated region will be symmetrical about the median antero-posterior plane of the endplate. The lateral side portions of the first elevated region are defined in one embodiment by arcs that terminate in sagittal planes of the endplate and are symmetrical about a coronal plane of the endplate. In another embodiment the lateral side portions of the first elevated region are defined by circular arcs that are centered on points lying in sagittal planes of the endplate. The second elevated region has a generally dome-shaped surface, and its planform may be a complete circle or may be somewhat truncated at either or both of the anterior or posterior margins. In any case, the laterally opposite side portions of the second or upper elevated region are defined by circular arcs having a common center located on the median plane of the endplate. This common center may be located at any position along the median plane that is permitted by the overall size of the second elevated region. In one embodiment of the invention the common center may be located at the centroid of the first elevated region. The second elevated region may center of the circular dome is located at the centroid of the first elevated region.

In certain embodiments of the prosthesis endplate of the invention, the vertebra-contacting surface may also be provided with a generally central antero-posterior fin or keel located on the median plane, to provide additional stability against torsional displacement of the prosthesis with respect to the vertebral body and/or expulsion or extrusion of the prosthesis from the intervertebral space.

The endplate may be constructed from any material conventionally used for intervertebral prostheses, e.g., stainless steel, titanium, and the like. It may be manufactured by any conventional process for forming such structures, e.g., by machining, assembling from component parts by welding, or the like.

The vertebra-contacting surface defined by the base plate and elevated regions of the intervertebral prosthesis endplate of the invention provides an approximation to the shape of the natural concave surface of the end of the vertebral body, thus providing, in itself, for greater post-implantation stability of the prosthesis. However, it is also according to the invention to prepare a recess or seat in the end of the vertebral body to provide a more accurately conforming surface for contact between the endplate and the vertebral body. In view of the overall shape of the endplate surface as described above, this seat for the prosthesis endplate can be prepared with a relatively small excavation of the vertebral bone, especially when prepared by the implantation method of the invention described more fully below.

The invention also comprises a method for forming a concave seat in the end of a vertebral body to receive an intervertebral prosthesis endplate of the invention, as well as tools for conveniently and accurately forming such a concave seat.

According to the implantation method of the invention, the surgical site is exposed by a conventional anterior approach. At least a central and anterior portion of the degenerated intervertebral disc is excised, according to the condition of the disc and the surgical exigencies. Appropriate distraction of the adjacent vertebrae is performed to provide suitable access to the implantation site. A bone rasp having a central guide post, or pivot, and a head appropriately sized to form the recessed seat and carrying an array of rasp teeth that will form the seat is then inserted into the intervertebral space. The central pivot post is then inserted into a corresponding hole in the vertebral endplate made either by using a guide post having a bone-piercing pointed end or by predrilling a guide hole, and the rasp head is oscillated about the guide post in a transverse plane by an anteriorly extending handle to abrade the vertebral body endplate to form the seat for the prosthesis endplate.

In order to form a recess complementary to the intervertebral prosthesis endplate as described above, the bone-abrading teeth on the rasp head should be arranged in a planform and be graded in length in various regions of the planform to form a seat generally complementary to the contour of the vertebra-contacting surface of the prosthesis endplate. For example, a bone rasp suitable for preparing a seat for an embodiment of the endplate that has a transverse dimension greater than an antero-posterior dimension will generally also have a tooth array having a planform with a greater medial-lateral dimension that antero-posterior dimension and a shape that will form a seat complementary to the prosthesis endplate. Typically such an array of teeth will include a circular central region around the guide post with the height of the teeth being symmetrically reduced with distance from the guide post, in order to form the central circular dome-shaped region of the recess. The array of teeth will also typically include a lateral region, located radially and laterally outside of the central circular region, which is laterally symmetrical about a central pane of the rasp head and has a planform that will produce a laterally elongated recess complementary to the first elevated region of the prosthesis endplate. To this end the laterally outermost teeth will be positioned, and their length will be defined and gradated, to form the lateral portion of the laterally elongated portion of the recess or endplate seat, i.e., the lateral teeth will be shorter than those that form the central domed region. When the rasp head is oscillated, these outermost teeth will evidently describe a circular arc at each lateral extremity whose angular extent is determined by the angle through which the rasp head is oscillated as well as the angular sector of the rasp head covered by the array of teeth. Laterally inwardly from the outermost teeth the planform of the lateral region will be designed to form the anterior and posterior limits of the elongated recess when the rasp head is oscillated to its maximum excursion from its initially centrally aligned position. Evidently, the dimensions of this inward portion of the lateral region of the array of teeth may be chosen to form any particularly selected shape for the portion of the elongated recess connecting the outermost circular arcs. Typically, the laterally inward portions of the planform of the tooth array will be designed to produce generally straight laterally-extending anterior and posterior walls wall connecting the lateral terminal arcs of the elongated recess. Typically, the rasp head will be oscillated through an arc having an excursion of 10-15 degrees on each side of its initial central position, thereby creating an elongated recess having laterally terminal circular arcs, centered on the pivot point, of about 20-30 degrees. Other sizes of arcs can be selected for appropriate reasons. If the lateral regions of the tooth array are also symmetrical about a transverse plane, it is evident that the pivot point will be located at a centroid of the elongated recess.

It is also possible to produce the recess or seat for the prosthesis endplate in two stages, using a series of bone rasps, one having a circular tooth array for forming the central circular dome-shaped region for receiving the second elevated region of the prosthesis endplate, and another rasp having a tooth array shaped to form the elongated recess for receiving the first, elongated elevated region of the prosthesis endplate.

Although it is advantageous to prepare a recess or seat in a vertebral body that is an exact fit for the vertebra-contacting surface of the prosthesis endplate, those skilled in the art will recognize that, due to the circumstances of the implantation procedure, an exact match cannot always be obtained. Nevertheless, some preparation of a seat or recess in a vertebral body will, in general be advantageous, and any such preparation is according to the invention.

In another aspect, the invention includes a method and apparatus for forming an antero-posterior medial groove in a vertebral endplate to receive an antero-posterior medial fin or keel of a prosthesis endplate. Although such fins or keels have been used as stabilizing features of intervertebral prostheses, formation of a groove in the vertebral body to receive such a fin has ordinarily involved forming an aperture in at least the anterior rim of strong cortical bone surrounding the vertebral body. According to the invention, a groove for receiving a fin of an intervertebral prosthesis is cut only in the interior portion of the end of the vertebral body, sparing the rim of cortical bone. Evidently such preservation of the cortical rim provides additional protection against extrusion or expulsion of the intervertebral prosthesis. The formation of such an interior medial groove in vertebral endplate is accomplished using a surgical tool having a head bearing a guide surface similar to that of the vertebra-contacting surface of the vertebral prosthesis endplate of the invention. The tool is inserted into the intervertebral space after the seat for the prosthesis endplate has been created by the use of the above-described bone rasp apparatus. The tool is thus aligned accurately with respect to the end of the vertebral body. The groove-making tool includes a retractable or stowable cutter that is reciprocated along an antero-posterior medial channel by means of an operating shaft extending anteriorly to be operated by the surgeon. The cutter is retracted or stowed in a protective element when the tool is inserted into the intervertebral space, thus bypassing the cortical bone. After the tool is in position, the cutter is deployed and reciprocated to for a groove that accepts the fin of the prosthesis endplate, but does not extend through the cortical bone rim of the vertebra. Accordingly, the intact cortical bone rim provides superior resistance to expulsion of the prosthesis.

Thus, according to the invention, an intervertebral prosthesis using one or both endplates according to the invention, together with the formation of a corresponding seat in the vertebral body provides for a highly congruent contact between the endplate and the vertebral body, thereby providing a superior stability of the prosthesis against failure modes such as subsidence, migration, and expulsion. The surgical method and tools for forming the seat for the prosthesis endplate contribute to the simplicity of the implantation procedure.

The intervertebral prosthesis endplate of the invention is suitable for use with any such prosthesis employing any appropriate core structure or mechanism to allow restored physiological motion of the spinal motion segment. It is particularly adaptable to an intervertebral disc prosthesis wherein the core component is an elastomeric element that allows normal physiological motion.

The invention will now be illustrated by the accompanying drawings showing the use of the endplate of the invention in a prosthesis having an elastomeric core element. The surgical tools are also illustrated. It will be understood that the illustrated embodiments are illustrative only, the scope of the invention being defined by the appended claims.

Figure 1B:
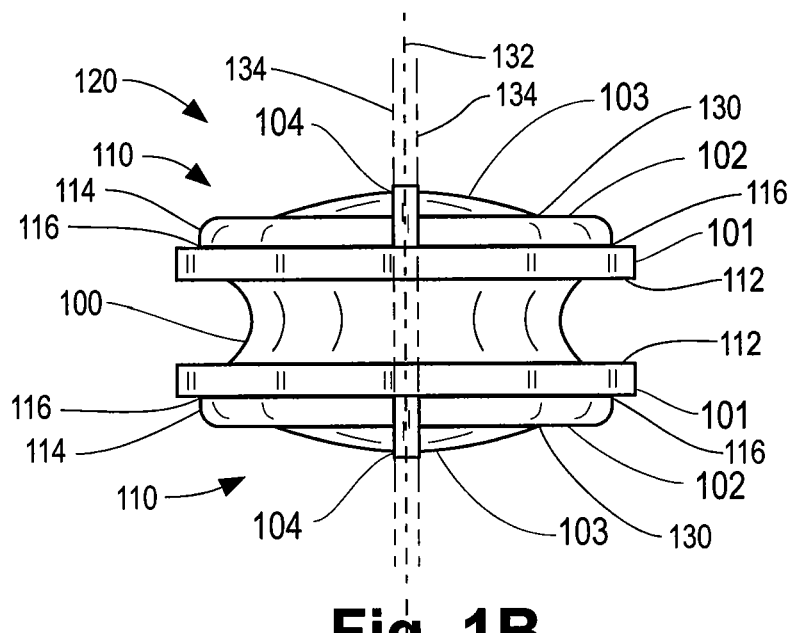
FIG. 1B is an anterior elevational view of an intervertebral prosthesis incorporating a prosthesis endplate of the invention taken in the direction 1B-1B in FIG. 1A.
Figure 1C:
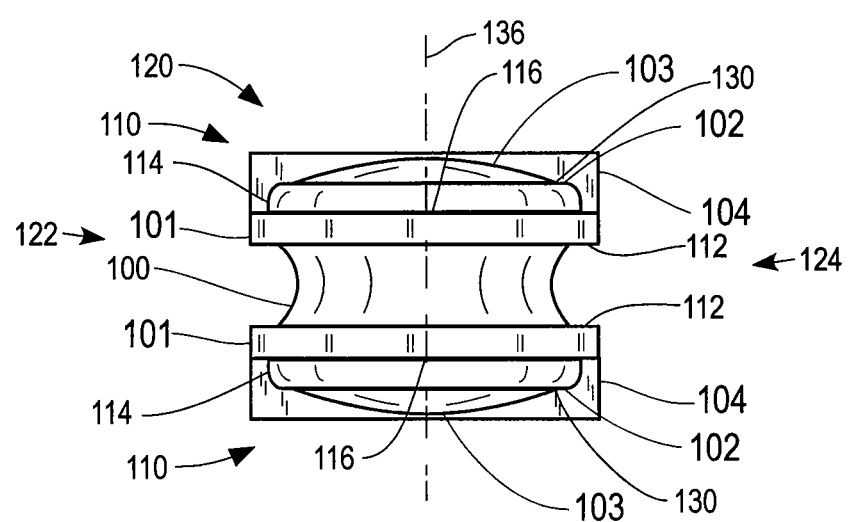
FIG. 1C is a lateral elevational view of the prosthesis of FIG. 1B, taken in the direction 1C-1C in FIG. 1A.

FIGS. 1A-1C illustrate a prosthesis endplate of the invention and its use in an intervertebral prosthesis having an elastomeric core element. The prosthesis has an elastomeric core element 100 and a pair of endplates 110 that are designed to contact the vertebral bodies of adjacent vertebrae in a human spinal motion segment. The prosthesis 120 has an anterior end 122 and a posterior end 124 as implanted in a spinal motion segment. Each of the endplates 110 comprises a base plate 112, a first elevated region 102, a second elevated region 103 and a medial fin 104. In order to illustrate the structure of the endplate 110 clearly, it is shown without the porous coating, e.g., of metallic beads, with which it is ordinarily provided in order to promote bone growth after implantation.

The base plate 112 has a peripheral rim 101, generally sized and configured to fit within the dimensions of an intervertebral space of a spinal motion segment. A first or lower elevated region or dome 102 is supported on the base plate 112 and has a wall or boundary 114, spaced radially inward from peripheral rim 101. The wall 114 has lateral extremities 116 generally in the shape of curved arcs 117 that terminate in sagittal planes 134. These arcs 117 are generally symmetrical about a coronal plane 136 of the endplate 110. The vertical profile of the first elevated region 102 may have varied shapes. For example, it may have a profile including a low wall and a generally planar elevated surface with a smooth transition therebetween. Alternatively, the profile of the first elevated region 102 may have a continuous constant or varied curvature from one extremity of the planform boundary 114 to the other in a lateral or antero-posterior orientation, with the evident proviso that such curvatures must be chosen to meet the planform boundary 114, which has a lateral dimension different from and typically greater than an antero-posterior dimension, as discussed above.

A second elevated region or dome 103 is supported on the first elevated region 102. The second elevated region 103, is bounded on its lateral portions by circular arcs 133 centered about a center point or axis 131 located on a median plane 132 of the endplate 110. The center point or axis 131 may also be located on the coronal plane 136, but does not have to be so positioned. In particular, the second elevated region 103 may have a generally circular planform 130, as shown. The second elevated region 103 typically has a vertical profile having a uniform curvature to provide a circular dome shape, as best seen in FIGS. 1B and 1C. The planform and curvatures of the second elevated region 103 may also be varied, within the parameters defined above, as discussed above for the first elevated region 102.

In the illustrated embodiment, the endplate 110 is provided with a medial fin 104, which is an optional element which may be included to provide for greater torsional stability of the prosthesis after implantation.

Figure 1D:
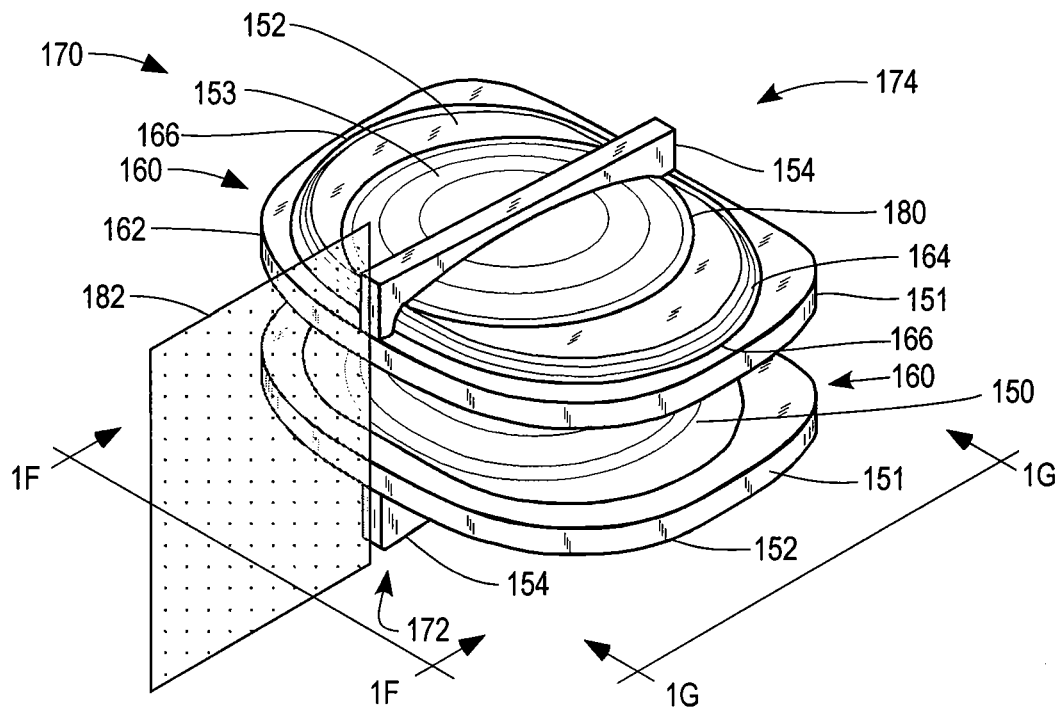
FIG. 1D is a perspective view of another embodiment of an intervertebral prosthesis incorporating a prosthesis endplate of the invention.
Figure 1E:
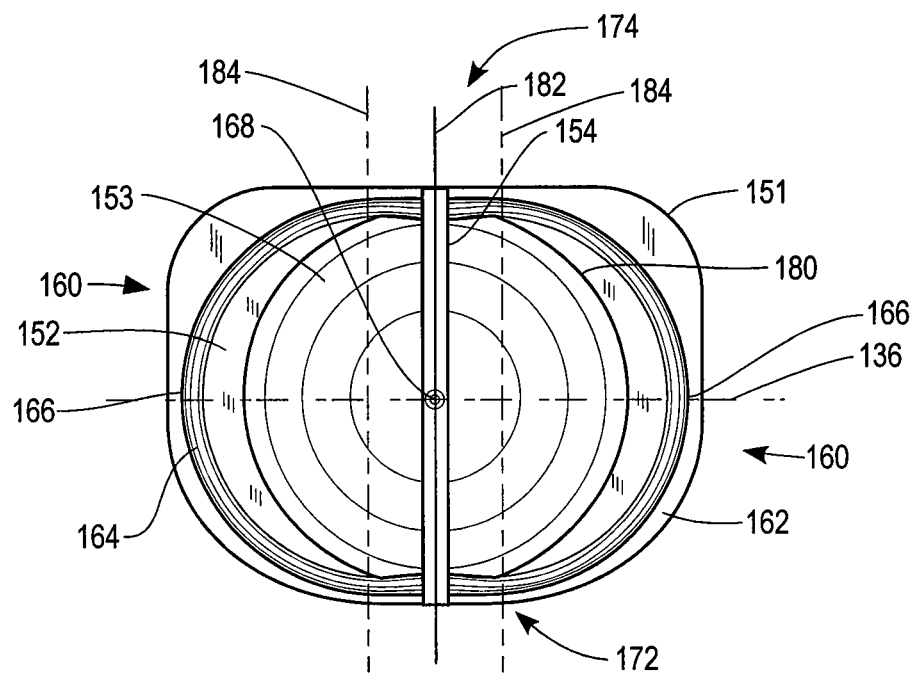
FIG. 1E is a plan view of the prosthesis of FIG. 1D.
Figure 1F:
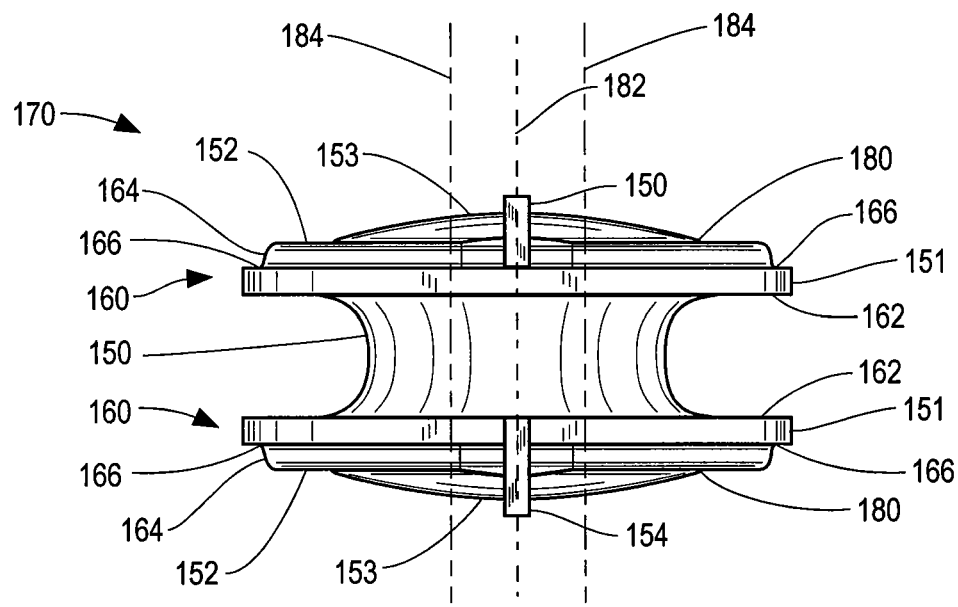
FIG. 1F is an anterior elevational view of the prosthesis of FIG. 1D, taken in the direction 1F-1F in FIG. 1D.
Figure 1G:
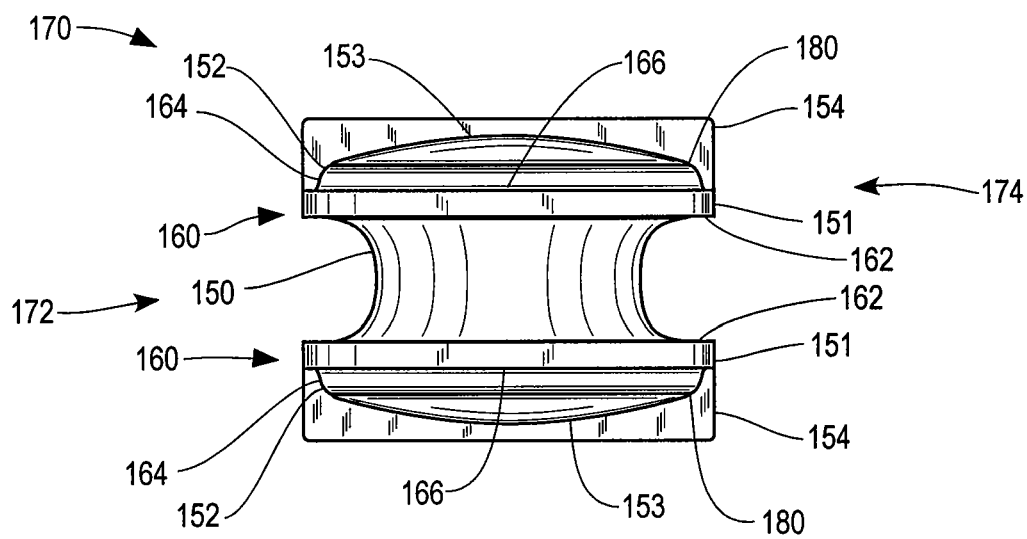
FIG. 1G is a lateral elevational view of the prosthesis of FIG. 1D, taken in the direction 1F-1F in FIG. 1D.

FIGS. 1D-1G illustrate another embodiment of the prosthesis endplate of the invention as used in a prosthesis 170 having an elastomeric core element. FIG. 1D illustrates a perspective view of such a prosthesis, while FIGS. 1E, 1F, and 1G illustrate plan, anterior elevational, and lateral elevational views, respectively.

The illustrated prosthesis 170 includes an elastomeric core 150 and two endplates 160. The prosthesis 170 has an anterior end 172 and a posterior end 174 as implanted in a spinal motion segment. The endplate 160 comprises a base plate 162, a first elevated region 152, a second elevated region 153 and a medial fin 154. In order to illustrate the structure of the endplate 160 clearly, it is shown without the porous coating, e.g., of metallic beads, with which it is ordinarily provided in order to promote bone growth after implantation.

The base plate 162 has a peripheral rim 151, generally sized and configured to fit within the dimensions of an intervertebral space of a spinal motion segment. A first or lower elevated region or dome 152 is supported on the base plate 162 and has a wall or boundary 164, spaced radially inward from peripheral rim 151. The wall 114 has lateral extremities 166 generally in the shape of circular arcs centered on a central or centroid 168 of the first elevated region 152. The vertical profile of the first elevated region 152 may have varied shapes. For example, it may have a profile including a low wall and a generally planar elevated surface with a smooth transition therebetween. Alternatively, the profile of the first elevated region 152 may have a continuous constant or varied curvature from one extremity of the planform boundary 164 to the other in a lateral or antero-posterior orientation, with the evident proviso that such curvatures must be chosen to meet the planform boundary 164, which has a lateral dimension greater than an antero-posterior dimension, as discussed above.

A second elevated region or dome 153 is supported on the first elevated region 152. The second elevated region 153 has a generally circular planform 180, with a uniform curvature to provide a circular dome shape. The planform and curvatures of the second elevated region 153 may also be varied, as discussed above for the first elevated region 152.

In the illustrated embodiment, the endplate 160 is provided with a medial fin 154, which is an optional element which may be included to provide for greater torsional stability.

The first elevated region and second elevated region are generally symmetrical with respect to a median plane 182, illustrated schematically in FIGS. 1D and 1*n* FIGS. 1E and 1F. The circular arc shape of the lateral extremities 166 of the wall or boundary 164 allows for ease of construction of a seat for the endplate 160 in the vertebral body, as discussed more fully below. The medial-lateral dimension of the first elevated region 152 is made greater than its antero-posterior dimension in order to provide stability against the possibility of torsional displacement of the prosthesis with respect to the vertebral body.

The second elevated region 153 typically has a generally circular planform in order to conform to the generally concave shape of the end of the vertebral body. However, the curvature of the second elevated region 153 may be varied substantially to conform to varying curvatures of the vertebral end structures, which may depend on the level of the disc being replaced and the size of the patient. In any event, such a general dome shape provides for forming a seat for the endplate 160 in an adjacent vertebral body while minimizing the amount of vertebral bone that has to be removed. The second elevated region 153 may also have any shape symmetrical with respect to median plane 182, as described above for the first elevated region 152. It is not excluded that in exceptional cases, e.g., where the seat for the endplate 160 in a vertebral body cannot be formed by symmetrical motion of a bone rasp, as discussed below, that the first and/or second elevated regions might not be completely symmetrical with respect to the median plane 182.

Certain advantages accrue to the above-described design of an endplate for an intervertebral prosthesis, particularly when compared with an endplate having a flat or single domed endplate. Thus, a flat surface evidently can provide limited mechanical stability against shear or translational motion of the prosthesis with respect to the vertebral body. A single dome, having similar anterior-posterior and medial-lateral dimensions, while it enhances prosthetic stability in shear or simple translation, remains limited in its ability to prevent rotation of the endplate with respect to the vertebral body. The inventive design, by having two elevated regions, or domes, at least one of which has different medial-lateral and antero-posterior dimensions, provides for enhanced stability in both translation and also in rotation. Furthermore, the relatively simple shapes of the elevated regions, which are adapted to the relatively simple and straightforward procedures and tools for formation of a complementary seat in the vertebral body, provide evident advantages over more complex shapes that could be devised to provide similar stability and would require complex surgical procedures for preparation and implantation.

FIGS. 2A-2H show the bone rasp tools and apparatus used to prepare the recess or seat for receiving the endplate of the invention.

Figure 2A:
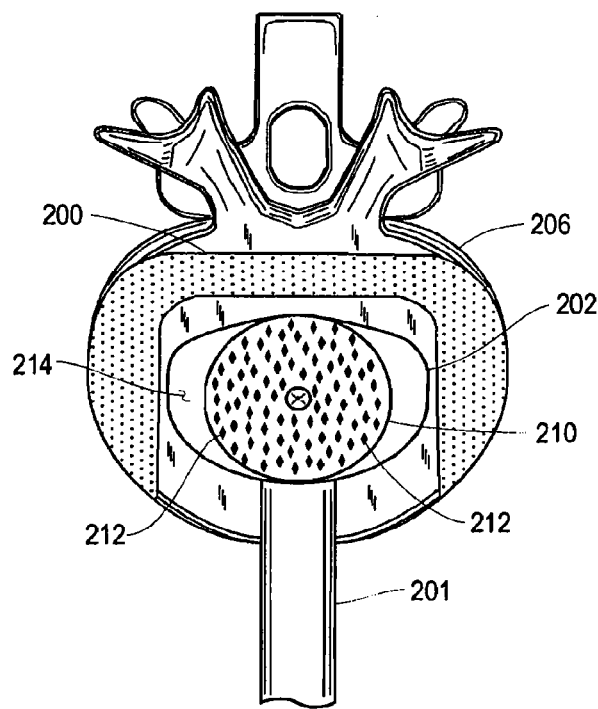
FIG. 2A is a superior view of an embodiment of a bone rasp of the invention positioned in an intervertebral space after excision of a central portion of the annulus fibrosus for preparation of a central portion of a recess or seat in the lower or caudal end of the superior vertebra (not shown).
Figure 2B:
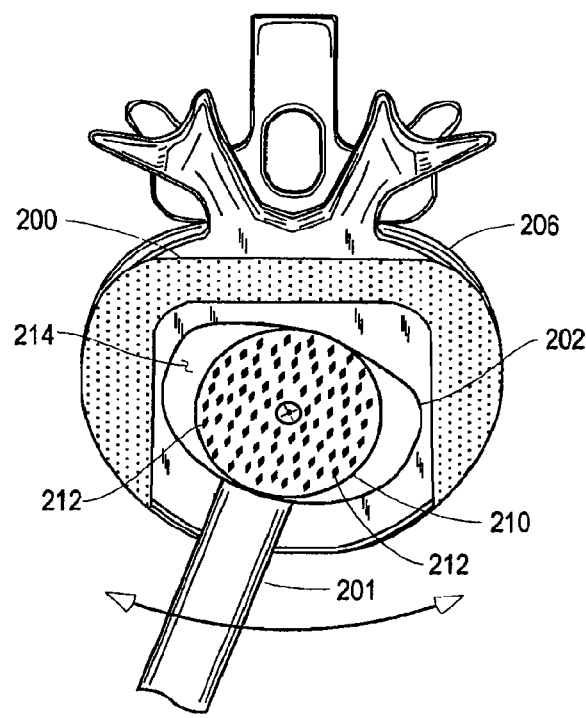
FIG. 2B shows the angular reciprocating motion of the rasp of FIG. 2A in preparing the recess in the superior vertebra.

FIG. 1A shows an embodiment of a bone rasp tool 201 having a rasp head 202 positioned within an intervertebral space between a lower, or caudal vertebra 206 of a spinal motion segment and the superior or cephalad vertebra (not shown) of the spinal motion segment. The central portion of the intervertebral disc has been excised leaving a residual portion 200 of the annulus fibrosus. The bone rasp head 202 has a central elevated region 210 having teeth 212 arranged to form the central portion of a recess or seat for receiving a prosthesis endplate of the invention. The rasp has a central projection or post to serve as a pivot about which the rasp head 202 can be moved in a reciprocating angular motion as indicated in FIG. 2B. The peripheral portion 214 of the rasp head 202 in this embodiment is devoid of teeth. Accordingly, this embodiment of the bone rasp is used in a first step to prepare the central region of the recess.

Figure 2C:
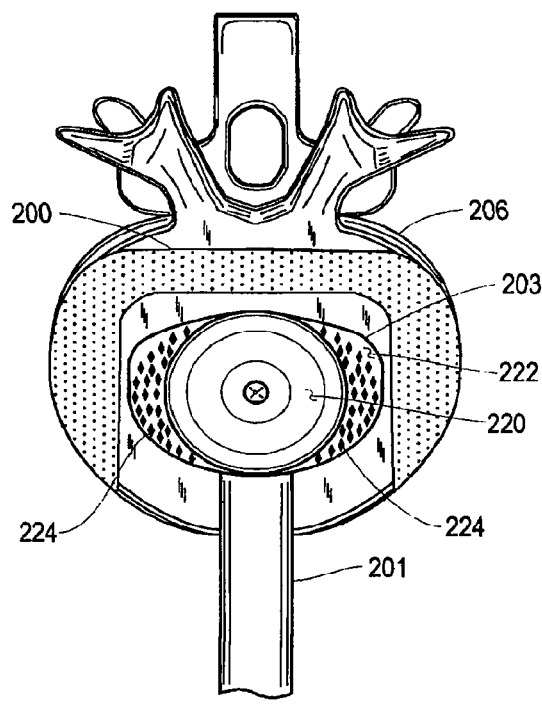
FIG. 2C shows a subsequent step in the preparation of a recess n the superior vertebra wherein a second bone rasp having teeth configured to form the peripheral portion of the recess has been inserted into the intervertebral space.
Figure 2D:
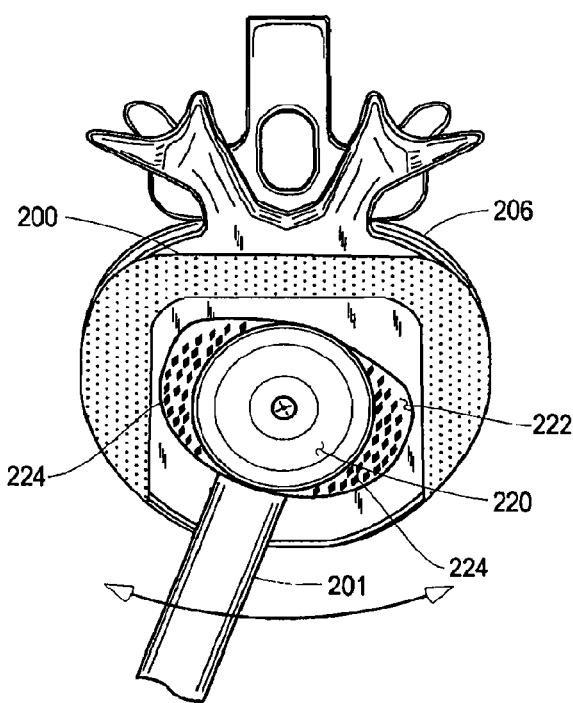
FIG. 2D shows the angular reciprocating motion of the rasp of FIG. 2C in preparing the peripheral portion of the recess in the superior vertebra.

FIG. 2C shows a second embodiment of a bone asp having a rasp head 203 positioned within a surgically prepared intervertebral space for forming the peripheral region of the recess. In this embodiment the central region 220 is devoid of teeth while the peripheral region 222 is provided with teeth 224 for preparing the peripheral region of the recess by angular reciprocating motion as shown in FIG. 2D.

Figure 2E:
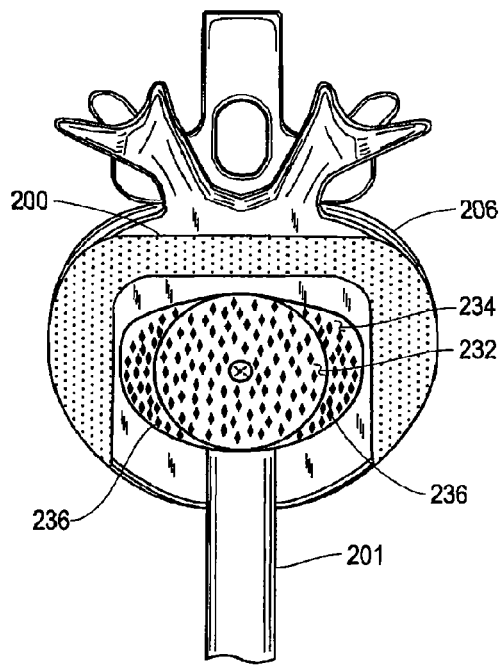
FIG. 2E shows an alternate embodiment of a bone rasp for preparing a recess in a vertebral body wherein teeth are arranged and configured to prepare the central and peripheral regions of the recess.

FIG. 2E shows an embodiment of the bone rasp having a head 230 wherein both the central region 232 and the peripheral region 234 are provided with teeth 236 for preparing both the central portion and peripheral portions of the recess at the same time.

Figure 2F:
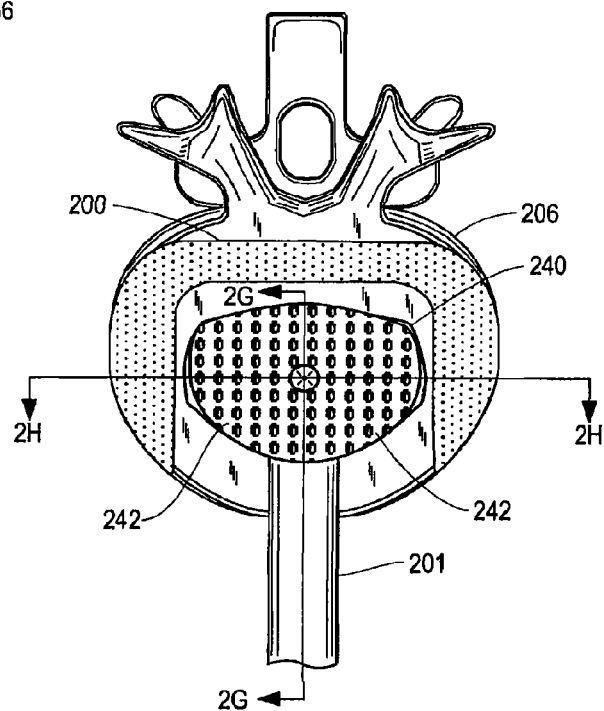
FIG. 2F shows another embodiment of the bone rasp for preparing a recess in a vertebral body wherein the teeth are arranged on a generally planar base and have different lengths for forming the shape of the recess, as seen more particularly in the cross-sections of FIGS. 2G and 2H.
Figure 2G:
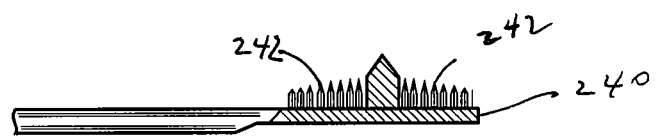
FIG. 2G shows a cross-section of the bone rasp of FIG. 2F, taken along the line 2G-2G.
Figure 2H:
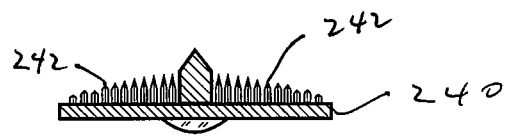
FIG. 2H shows a cross-section of the bone rasp of FIG. 2F, taken along the line 2H-2H.

FIG. 2F shows another embodiment of the bone rasp having a head 240 positioned with in a surgically prepared intervertebral space. The head 240 is provided with teeth 242 of differing lengths in differing regions of the head 240, as illustrated in the cross sections FIGS. 2G and 2H, for preparing the central and peripheral regions of the recess at the same time.

Figure 3A:
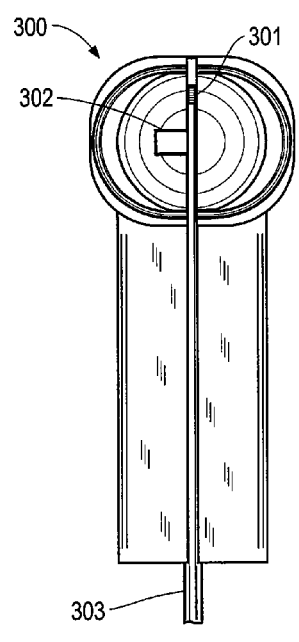
FIG. 3A is a plan view of a groove-cutting instrument used to cut a groove within the vertebral body to receive a fin of a prosthesis endplate according to the invention, wherein the cutting element of the instrument is in cutting position.
Figure 3B:
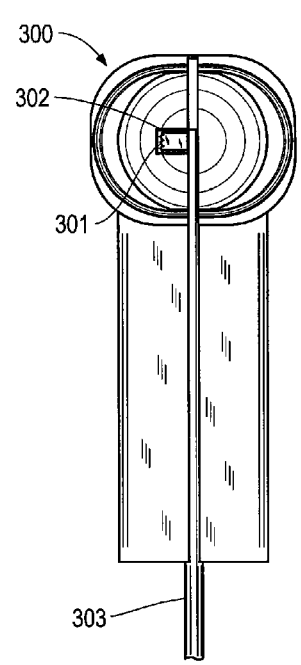
FIG. 3B is a plan view of the groove cutter of FIG. 3A wherein the cutting element is retracted into a recess for insertion of the instrument into an intervertebral space.
Figure 3C:
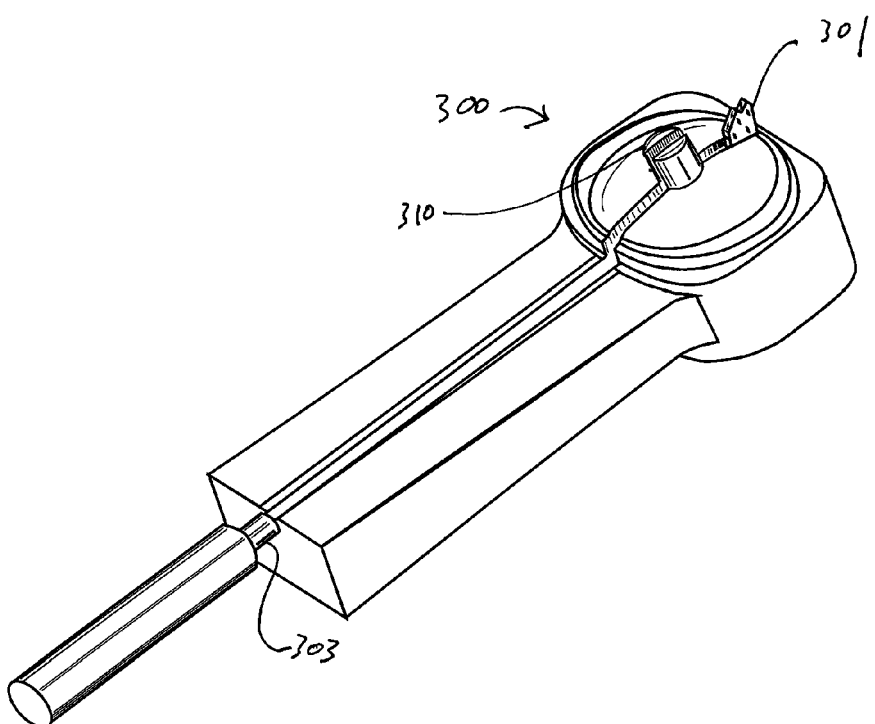
FIG. 3C is a perspective view of the groove cutter of FIGS. 3A and 3B.

FIGS. 3A-3C illustrate a groove-cutting tool that can be used to prepare the anterior-posterior groove to receive a prosthesis fin, e.g., the fin 104. This tool 300 is inserted into the disc cavity after the various rasps have been used and employs a side-cutting edge 301 to prepare a groove on both the superior and inferior surfaces. The tool 300 is introduced with the cutting edge 301 rotated such it does not protrude above the top surface but rather lies flat within the recess 302, as shown in FIG. 3B. Alternatively, the tool can be provided with a center guidepost 310, as shown in FIG. 3C, which serves both to position the groove-cutting tool within the intervertebral space and to stow the cutter in a place where it will not damage bone or other tissue when the tool 300 is inserted. Once the tool 300 in place, the shaft 303 is rotated a quarter turn and the edge cutter 301 is exposed. The shaft 303 is then reciprocated causing the edge cutter 301 to prepare the appropriate slot in the vertebra. The inferior vertebra is prepared in a similar fashion. An alternate design provides for edge cutters on both superior and inferior surfaces of the tool so that both slots are prepared in a single operation.

The invention having been described in terms of certain embodiments, it will be apparent to those skilled in this art that many changes and alterations can be made without departing from the spirit or essential characteristics of the invention. The present disclosure is therefore to be considered as illustrative, and not restrictive, of the invention.

We claim:

1. A bone rasp apparatus configured to form a recess of predetermined configuration in a vertebral body, comprising at least one bone rasp tool including:
   a rasp head, and
   a handle,
   said rasp head having:
      a pivot member, and rasp teeth arranged to prepare at least a portion of said recess by reciprocal pivotal rotation of said rasp head about said pivot member, the rasp teeth configured to form:
   a first recessed region having an antero-posterior dimension and a transverse dimension different from said antero-posterior dimension and being bounded by a wall with opposite lateral side portions defined by circular arcs centered on sagittal planes of said vertebral body, and a second, generally dome-shaped, recessed region within said first recessed region, said second recessed region having lateral sides defined by circular arcs centered on a center point in a median plane of said vertebral body.

2. The bone rasp apparatus of claim 1, wherein said rasp teeth are arranged to form a recessed region having an antero-posterior dimension and a transverse dimension different from said antero-posterior dimension and being bounded by a wall with opposite lateral side portions defined by circular arcs centered on sagittal planes of said vertebra.

3. The bone rasp apparatus of claim 1, wherein said transverse dimension is greater than said antero-posterior dimension.

4. The bone rasp apparatus of claim 1, wherein said rasp teeth are arranged to form a generally dome-shaped recess having a circular planform.

5. The bone rasp apparatus of claim 1, wherein said transverse dimension is greater than said antero-posterior dimension.

* * * * *